(12) United States Patent
Kimm et al.

(10) Patent No.: US 10,692,609 B2
(45) Date of Patent: Jun. 23, 2020

(54) METHOD FOR PRODUCING AN ORTHOSIS

(71) Applicant: EOS GmbH Electro Optical Systems, Krailling (DE)

(72) Inventors: Martin Kimm, Aachen (DE); Vincent Antoine, München (DE)

(73) Assignee: EOS GmbH Electro Optical Systems, Krailling (DE)

( * ) Notice: Subject to any disclaimer, the term of this patent is extended or adjusted under 35 U.S.C. 154(b) by 400 days.

(21) Appl. No.: 15/560,217

(22) PCT Filed: Mar. 23, 2016

(86) PCT No.: PCT/EP2016/056394
§ 371 (c)(1),
(2) Date: Sep. 21, 2017

(87) PCT Pub. No.: WO2016/151020
PCT Pub. Date: Sep. 29, 2016

(65) Prior Publication Data
US 2018/0046775 A1  Feb. 15, 2018

(30) Foreign Application Priority Data
Mar. 25, 2015  (DE) .......................... 10 2015 003 819

(51) Int. Cl.
*A61F 5/01*  (2006.01)
*G16H 50/50*  (2018.01)
(Continued)

(52) U.S. Cl.
CPC ............ *G16H 50/50* (2018.01); *A61B 5/1079* (2013.01); *A61F 5/0102* (2013.01); *A61F 5/013* (2013.01); *A61F 2002/5049* (2013.01)

(58) Field of Classification Search
CPC ..... G16H 50/50; A61B 5/1079; A61F 5/0102; A61F 5/013; A61F 5/0118;
(Continued)

(56) References Cited

U.S. PATENT DOCUMENTS

2013/0226533 A1* 8/2013 Summit ................ A61F 2/5046
703/1

FOREIGN PATENT DOCUMENTS

| WO | 20090015455 | 2/2009 |
| WO | 20100111768 | 10/2010 |
| WO | 20130142343 | 9/2013 |

OTHER PUBLICATIONS

International Search Report for PCT Application No. PCT/EP2016/056394, dated Sep. 6, 2016, 12 pages.

* cited by examiner

*Primary Examiner* — Ophelia A Hawthorne
(74) *Attorney, Agent, or Firm* — Seyfarth Shaw LLP

(57) ABSTRACT

A method for producing an orthosis includes at least the steps of receiving patient data of at least one body part of a patient, wherein the body part is borne substantially without a holding apparatus during the reception, ascertaining and/or receiving reference coordinates of virtual and/or physical target objects on the body part, wherein the body part is borne substantially without a holding apparatus during the ascertainment and/or reception and wherein the target objects represent at least one location on the surface of the body part that is representative for attaching the orthosis on the body part, individually fitting a digital orthosis model on the basis of the patient data and the reference coordinates, and manufacturing the orthosis on the basis of the digital orthosis model that is fitted in this way.

8 Claims, 1 Drawing Sheet

(51) Int. Cl.
  *A61B 5/107* (2006.01)
  *A61F 2/50* (2006.01)
(58) Field of Classification Search
  CPC .... A61F 5/05875; A61F 5/10; A61F 5/05866;
    A61F 2007/0037; A61F 5/01; A61F
    2007/0098; A61F 13/041; A61F
    2007/0233; A61F 2007/0242; A61F
    9/00745; A61F 5/50; A61F 2/5046; A61F
    2/50; A61F 2002/505; B33Y 50/00; G06T
    19/00; G06T 2210/41
  See application file for complete search history.

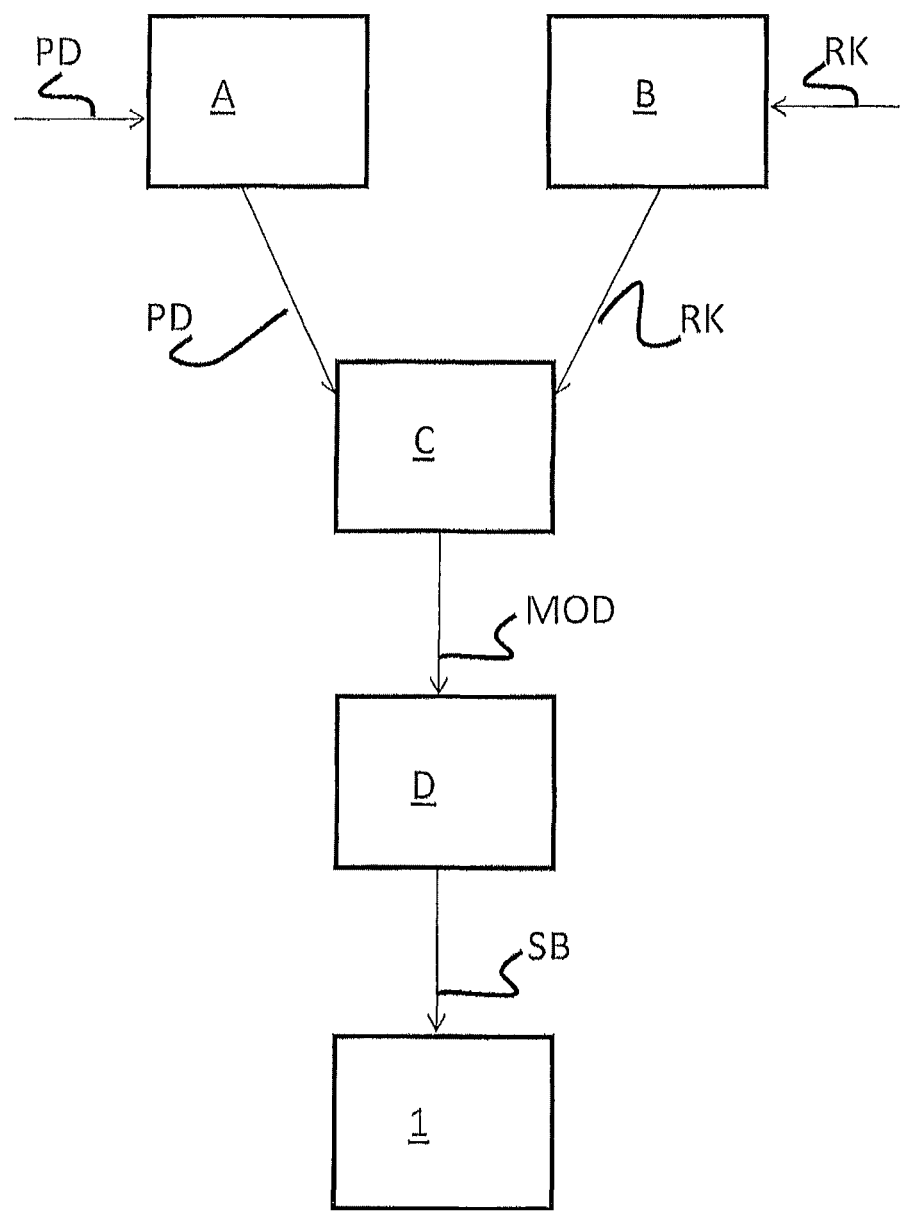

METHOD FOR PRODUCING AN ORTHOSIS

TECHNICAL FIELD OF THE INVENTION

The invention relates to a method for producing an orthosis.

BACKGROUND OF THE INVENTION

Orthoses serve to correct malpositions of body parts such as e.g. arms, legs or the torso. For the purposes of producing an orthosis, a copy of the affected body part, for example a forearm, of the patient was previously manufactured by virtue of initially taking a plaster cast of the body part in the desired correction position. Thereupon, the orthosis contour was produced on the plaster model in a deep drawing or laminating process by virtue of a heated plastic plate being placed around the plaster model. Subsequently, the plastic was removed from the plaster form in a grinding workshop. Here, the inner plaster core was e.g. broken away by a hammer drill with a chisel attachment and the contour of the orthosis was cut out. After removing the inner core and approximately cutting out the spiral contour, the cut edges had to be post-processed by a number of grinding processes. This was carried out first by an approximate grinding process and then by final smoothing to form the intended contour. Furthermore, the inner surfaces were provided with an attached lining for increasing the comfort of wear. Thereupon, the orthosis could be matched to the forearm of the patient by a qualified orthopedist. Points at which there was increased pressure on the skin or edges that cut into the skin could subsequently be removed by polishing or by means of local heating.

However, this conventional production method has a number of disadvantages. The geometry of the model is, as a rule, over-dimensioned due to the plaster cast method, as a result of which an approximation to the original dimensions must be effectuated during the modeling. Further, there can be gross manufacturing inaccuracies as a result of the manual production, leading to an uneven contact face on the body part of the patient. As a result of this, local pressure points may arise on the skin which, over a relatively long period of time, are perceived to be particularly uncomfortable, up to a painful feeling.

Moreover, the described production process is complicated as it is hardly possible to resort to standard components. Each work step is undertaken manually, in particular as a result of the necessary, high individualization of the individual products and the relatively low number of units when compared with other industry sectors. This significantly increases both the production costs and the time outlay for the production. In parallel with this, the reproducibility of the individual measures is made more difficult.

Since the entire production process is carried out by hand, it is not possible to ensure a high surface accuracy. In particular, manufacturing the body part copy from plaster may cause significant form deviations of several millimeters. In the subsequent processing of this plaster copy, material is additionally removed and applied according to the empirical knowledge of the orthopedist in order to smooth the surface and rectify impression errors. In so doing, the original contour can only be reproduced approximately.

Moreover, an unchanging correction quality cannot be ensured during manufacturing. As a rule, the orthosis must be post-corrected again when it is tried on the patient. Moreover, it is not clear at the end of the manufacturing process whether the correction position that was set at the outset by the plaster cast could be accurately achieved.

Consequently, the main cause of the manufacturing tolerances that occur is, firstly, the practice of manufacturing the body part copy from plaster, which produces significant form deviations of several millimeters. Secondly, the subsequent processing steps should be assigned to the handiwork of the respective modeler, which has an effect on the comprehensible documentation and manufacturing quality.

SUMMARY OF THE INVENTION

It is therefore an object of the present invention to develop an improved method, by means of which an orthosis can be constructed, simulated and produced from defined characteristics. In particular, such an improvement is directed to solving as many of the above-described problems in the prior art as possible and/or contributing to a higher supply quality or precision, and a structured procedure and reproducibility, in all manufacturing stages.

The object is achieved by a method for producing an orthosis according to claim 1. The invention also relates to an orthosis that was produced by means of this method, said orthosis being able to be developed in accordance with all the dependent claims of the method. In addition, the method may be developed in accordance with the dependent claims relating to the orthosis.

In theory, it is possible to obtain patient data of the relevant body part of the patient while the corresponding body part is held in a holding apparatus. Such a holding apparatus could hold the body part in an adjustable correction position and, for example, have a plurality of holding regions and one or more correction force setting apparatuses, with at least one of the correction force setting apparatuses being connected to at least one of the holding regions. Using the correction force setting apparatuses, correction forces could be exertable on the body part via the holding regions that are connected to the correction force setting apparatuses and, as a result of this, the body part could be brought into a correction position.

The present invention deliberately does not make use of this principle; instead, it is based, inter alia, on the corresponding body part being borne substantially without a holding apparatus. Thus, no holding apparatus of the type set forth above is used; "without a holding apparatus" accordingly is the opposite to the use of such a holding apparatus as described in the previous paragraph.

Thus, the corresponding body part may be borne, for example, by simply placing the body part onto a surface and/or by the patient independently holding the body part themselves. The desired position of the body part may be obtained, in this case, by the form of this surface (which preferably comprises a flat plane) and/or by the patient holding the body part deliberately and/or naturally. In this context, holding the body part serves only for temporary stationary fixation, if at all, for example in a medical imaging device (see below). More detailed exemplary specifications in respect of possible attainment of the desired body part positions are likewise found below.

Thus, according to the invention, a method for producing an orthosis comprises at least the following steps:

receiving patient data of at least one body part of a patient, wherein the body part is borne substantially without a holding apparatus during the reception, ascertaining and/or receiving reference coordinates of virtual and/or physical target objects on the body part, wherein the body part is borne substantially without a holding apparatus during the ascertainment and/or reception and wherein the target objects represent at least one location on the surface of the body part that is representative for attaching the orthosis on the body part, individually fitting a digital orthosis model on the basis of the patient data and the reference coordinates, manufacturing the orthosis, in particular at least in part with the aid of an additive manufacturing method, on the basis of the digital orthosis model that is fitted in this way.

In principle, it is possible within the scope of the method according to the invention that the patient data and/or the reference coordinates are ascertained or derived, wholly or in part, from a medical imaging method, for example an MRI or CT scan, an x-ray image recording or similar medical imaging methods. This applies, firstly, to the patient data and, secondly, to the reference coordinates of the target objects as well. The corresponding body part or even the whole body of the patient is borne within the scope of such a medical imaging method and, in the process, possibly also temporarily fixed within the aforementioned meaning.

Alternatively, or in a complementary manner, the patient data and/or the reference coordinates may be received or ascertained, wholly or in part, by virtue of the patient being instructed to assume a specific position with the respective body part and/or to carry out a predetermined sequence of movements. By way of example, said patient can be instructed to lift their arm, on which the corresponding orthosis should be fitted, and move the fingers on the corresponding hand into specific positions in accordance with a predetermined pattern, or to keep the fingers at said positions. The positions of the arm, i.e. of the body part in general, and/or of the fingers, i.e. of portions of the body part in general, into which these should be transferred in each case are preferably limit positions, i.e. the positions beyond which the patient can move the corresponding body part or the respective portion thereof only by overcoming relatively strong physical resistance or under pain. The patient data that are obtained thus then also represent limit data in respect of the movement capability of the corresponding body part or portion. These limit data are very preferably included when adapting the digital orthosis model.

"Virtual target objects" are understood to mean, in particular, those target objects which are or were provided to the patient data—for example as a digital additional input. By way of example, these include markers which mark and denote a specific location or a specific partial object of the relevant body part. Such a provision can be effectuated manually, for example by a treating practitioner or a practitioner who evaluates the findings, but it may also be carried out in an automated fashion, for example by an automated identification algorithm which carries out an object identification (e.g. in the form of a segmentation of a specific body structure) on the basis of the patient data and which places corresponding markers.

"Physical target objects" are those objects which are physically attached to the relevant body part of the patient. By way of example, in this case, this may relate to marks with symbols, signs or the like on the surface of the body part, for example location marks on the skin of the patient that have been painted on.

In particular, the target objects comprise physical target objects, in particular anchoring pads, which are applied to the surface of the body part during a scan of the body part. Then, the patient data comprise scan data from this scan. This ensures that the reference coordinates of the physical target objects are exactly matched to the patient data. Here, anchoring pads can serve to define a location at which the respective patient has skin contact with the orthosis when wearing the orthosis that is produced according to the invention. Thus, such anchoring pads represent cushioning of the orthosis in relation to the skin of the patient, in particular the position and/or dimensions of such cushioning. Expressed differently: positions of the anchoring pads comprise potential contact positions between the body part and the orthosis to be manufactured.

Furthermore, it is preferable that a load distribution on account of opposing forces exerted by the body part in reaction to correction forces along the digital orthosis model are calculated and/or simulated in a state substantially without a holding apparatus, the geometry of the orthosis is optimized in the digital orthosis model in accordance with the calculated and/or simulated load distribution, and/or a perforation and/or lattice structure in the digital orthosis model is generated in accordance with the calculated and/or simulated load distribution. Such a calculation or simulation is preferably substantially based on an evaluation, in particular an at least partly automated evaluation, of the relevant patient data.

In this context, it should be mentioned that the patient data need not necessarily comprise purely static image data within the meaning of a snapshot in time but may also, for example, be provided in the form of moving image data, i.e. in the style of a video sequence or sequence. Such a sequence then for example represents a sequence of movement of the corresponding body part pictorially, and from this sequence of movement certain movement patterns or movement obstacles of the body part can easily be derived, modeled and, ultimately, simulated, in particular in a manner based on an algorithm.

An orthosis for correcting a malposition of a body part also lies within the scope of the invention, wherein this orthosis is produced by means of an above-described method for producing an orthosis.

Further, the orthosis that is produced in this way may, in regions or overall, have a perforated structure and/or a lattice structure which, at least in regions, is adapted in accordance with the calculated and/or simulated load distribution. The lattice structure may have an open or closed embodiment. In the case of the open lattice structure, the lattice structure has lattice openings that are delimited by a lattice. In the case of the closed lattice structure, the lattice openings are closed by a material layer which has a lower material strength than, or the same material strength as, the lattice.

The orthosis can be manufactured to be lighter by using a lattice structure, while the stability stays unchanged. Additionally, the open lattice structure facilitates good ventilation of a body part that is held by the orthosis. This increases the comfort of wear of the orthosis. At the same time, the use of an open lattice structure opens up multifaceted design options, as a result of which the acceptance of the orthosis by the patient is in turn improved.

In a preferred configuration of the orthosis, the lattice structure has a bone cell structure and/or a Voronoi structure. These structures are particularly stable while having a comparatively low material outlay.

The lattice structure can be a two-dimensional lattice which extends in the tangential direction, i.e. parallel to the surface of a body part when the orthosis is placed thereon. Further, it may be advantageous if the orthosis, either in regions or overall, has a wall with one or more layers, in particular two or three layers, and if the number of layers along the orthosis varies or remains constant. In this case, the wall may be e.g. a three-dimensional lattice structure which has at least one further lattice plane (second layer) in the radial direction, i.e. in a direction that is perpendicular to the surface of a body part when the orthosis is placed thereon, said at least one further lattice plane likewise extending in the tangential direction. It is also conceivable for the lattice structure, in various regions of the orthosis, to have a different number of lattice planes (layers) that are arranged in the radial direction and extend in the tangential direction. Further, the number of these lattice planes (layers) may vary in the tangential direction of the orthosis. Preferably, the wall of the orthosis has a larger number of layers in strongly strained regions of the orthosis than in less strongly strained regions of the orthosis. In this way, it is possible to form soft areas in the orthosis in order to guide bone movements in a bedded manner.

BRIEF DESCRIPTION OF THE DRAWINGS

Below, an example of a method according to the invention for producing an orthosis is described in more detail on the basis of a FIGURE. In detail:

FIG. 1 shows, in a block diagram, an exemplary embodiment of a production method according to the invention.

DETAILED DESCRIPTION OF THE EMBODIMENTS

In a first step A, patient data PD of at least one body part of a patient, for example patient data PD of a forearm, are received. These patient data may originate from practically any imaging method, in particular a photographic or sensing-based scan or a medical imaging scan. In a second step B, reference coordinates RK of virtual or physical target objects on the body part are ascertained or received. Both steps A and B are effectuated substantially without a holding apparatus within the aforementioned meaning.

In a third step C, there is an individual adaptation of a digital orthosis model (which for example is already present in an ideal-typical form of an initial model) on the basis of the patient data PD and the reference coordinates RK. By way of example, for the start point of adapting the orthosis model, it is possible to select from ideal-typical forms of a respective body part of a child, a female adult, and a male adult (however, in principle, it could also be possible to take animal patients into account such that the ideal-typical form of the initial model then preferably relates to the respective species, breed or the like of the relevant animal). The result of the third step C is a fitted orthosis model MOD, on the basis of which the following may now be effectuated in a fourth step D, which may also occur separated in time and/or space from the previously effectuated steps:

In step D, the orthosis 1 for the respective body part that corresponds to the fitted orthosis model is manufactured, preferably using an additive manufacturing method.

Steps A, B, and C are also not necessarily directly coupled to one another in space and/or time but may instead also be carried out separately from one another in each case.

The invention claimed is:

1. A method for producing an orthosis, comprising at least the following steps:
   receiving patient data of at least one body part of a patient, wherein the body part is borne substantially without a holding apparatus during the reception;
   ascertaining and/or receiving reference coordinates of virtual and/or physical target objects on the body part, wherein the body part is borne substantially without a holding apparatus during the ascertainment and/or reception and wherein the target objects represent at least one location on a surface of the body part that is representative for attaching the orthosis on the body part;
   individually fitting a digital orthosis model on the basis of the patient data and the reference coordinates;
   manufacturing the orthosis based on the digital orthosis model;
   calculating and/or simulating a load distribution on account of opposing forces exerted by the body part in reaction to correction forces along the digital orthosis model, in a state substantially without a holding apparatus, and optimizing a geometry of the orthosis in the digital orthosis model according to the calculated and/or simulated load distribution; and/or
   calculating and/or simulating the load distribution on account of opposing forces exerted by the body part in reaction to correction forces along the digital orthosis model, in the state substantially without a holding apparatus, and generating a perforation and/or lattice structure in the digital orthosis model in accordance with the calculated and/or simulated load distribution.

2. An orthosis for correcting a malposition of a body part, produced by the method as claimed in claim 1.

3. The orthosis as claimed in claim 2, wherein the orthosis has a the perforation and/or the lattice structure which, at least in regions, is adapted in accordance with the calculated and/or simulated load distribution.

4. The orthosis as claimed in claim 3, wherein the lattice structure has a bone cell structure and/or a Voronoi structure.

5. The orthosis as claimed in claim 3, wherein the orthosis has, at least in a region of the orthosis, a wall with one or more layers, and the number of layers varies or is constant along the orthosis.

6. The method as claimed in claim 1, wherein the target objects comprise physical target objects, which are applied to the surface of the body part during a scanning of the body part, and the patient data comprise scan data from the scanning of the body part.

7. The method as claimed in claim 6, wherein the physical target objects comprise anchoring pads, and wherein positions of the anchoring pads comprise potential contact positions of the body part with the orthosis to be manufactured.

8. The method as claimed in claim 1, wherein the step of manufacturing is carried out at least in part with the aid of an additive manufacturing method.

* * * * *